United States Patent [19]

Spector

[11] Patent Number: 4,695,435

[45] Date of Patent: * Sep. 22, 1987

[54] LIGHT-ACTIVATED AROMA GENERATOR

[76] Inventor: Donald Spector, 380 Mountain Rd., Union City, N.J. 07087

[*] Notice: The portion of the term of this patent subsequent to Feb. 4, 2003 has been disclaimed.

[21] Appl. No.: 765,152

[22] Filed: Aug. 13, 1985

Related U.S. Application Data

[63] Continuation-in-part of Ser. No. 592,915, Mar. 23, 1984, Pat. No. 4,568,521.

[51] Int. Cl.$^4$ ............................................. A61L 9/2
[52] U.S. Cl. ................................... 422/124; 239/54; 239/55; 361/173; 422/4; 422/5; 422/105
[58] Field of Search ............... 422/105, 4, 5, 124; 362/96, 101; 239/54, 55; 361/173, 174, 175

[56] References Cited

U.S. PATENT DOCUMENTS

| | | | |
|---|---|---|---|
| 1,957,509 | 5/1934 | Vallen | 361/175 |
| 2,050,773 | 8/1936 | Wall | 422/124 |
| 2,986,689 | 5/1961 | Hofer | 361/173 |
| 3,353,191 | 11/1967 | Dahly | 136/291 |
| 3,609,450 | 9/1971 | Hart | 250/215 |
| 3,948,445 | 4/1976 | Andeweg | 422/125 |
| 4,242,831 | 1/1981 | O'Shaughnessy | 361/175 |
| 4,301,095 | 11/1981 | Mettler et al. | 422/124 |
| 4,346,059 | 8/1982 | Spector | 422/4 |
| 4,444,720 | 4/1984 | Mayer | 422/4 |
| 4,568,521 | 2/1986 | Spector | 422/124 |

Primary Examiner—Barry S. Richman
Assistant Examiner—William R. Johnson
Attorney, Agent, or Firm—Michael Ebert

[57] ABSTRACT

An aroma generator that is rendered operative only when one turns on an electric light bulb in the room in which the generator is installed, the generator then functioning to discharge an air current into the room conveying an aromatic vapor which modifies the prevailing atmosphere. Included in the generator is a motor-driven fan that forces air through an air permeable cartridge containing an aroma supply, the motor being connected to a battery through a signal-responsive electronic relay. Applied to the relay is a signal derived from a light sensor which is adjacent the light source to intercept light rays therefrom. The arrangement is such that when the bulb is switched on, the signal from the sensor is then of sufficient magnitude to actuate the relay and thereby render the generator operative, whereby the operation of the aroma generator is coordinated with that of the bulb without any wire connection therebetween.

7 Claims, 4 Drawing Figures

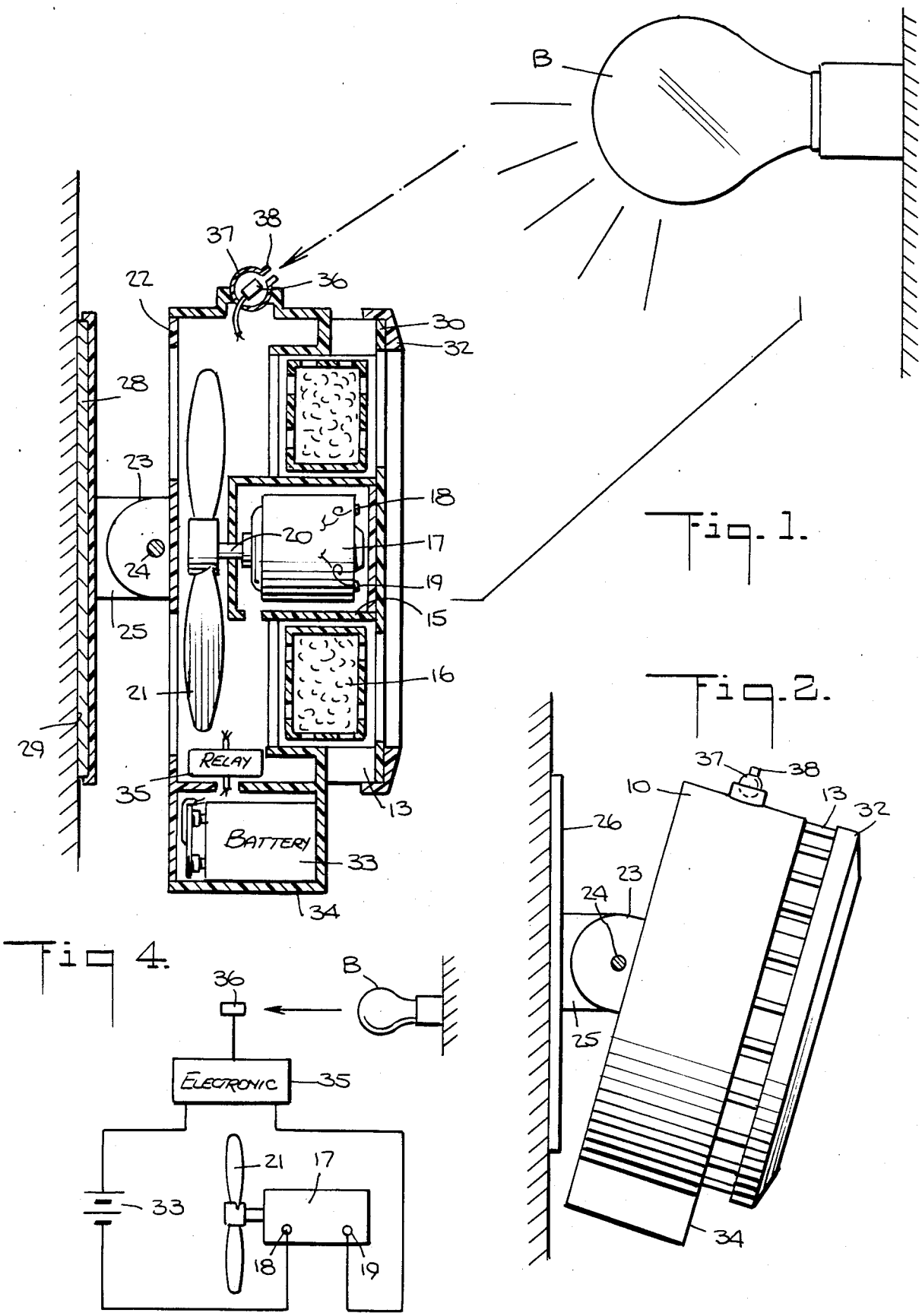

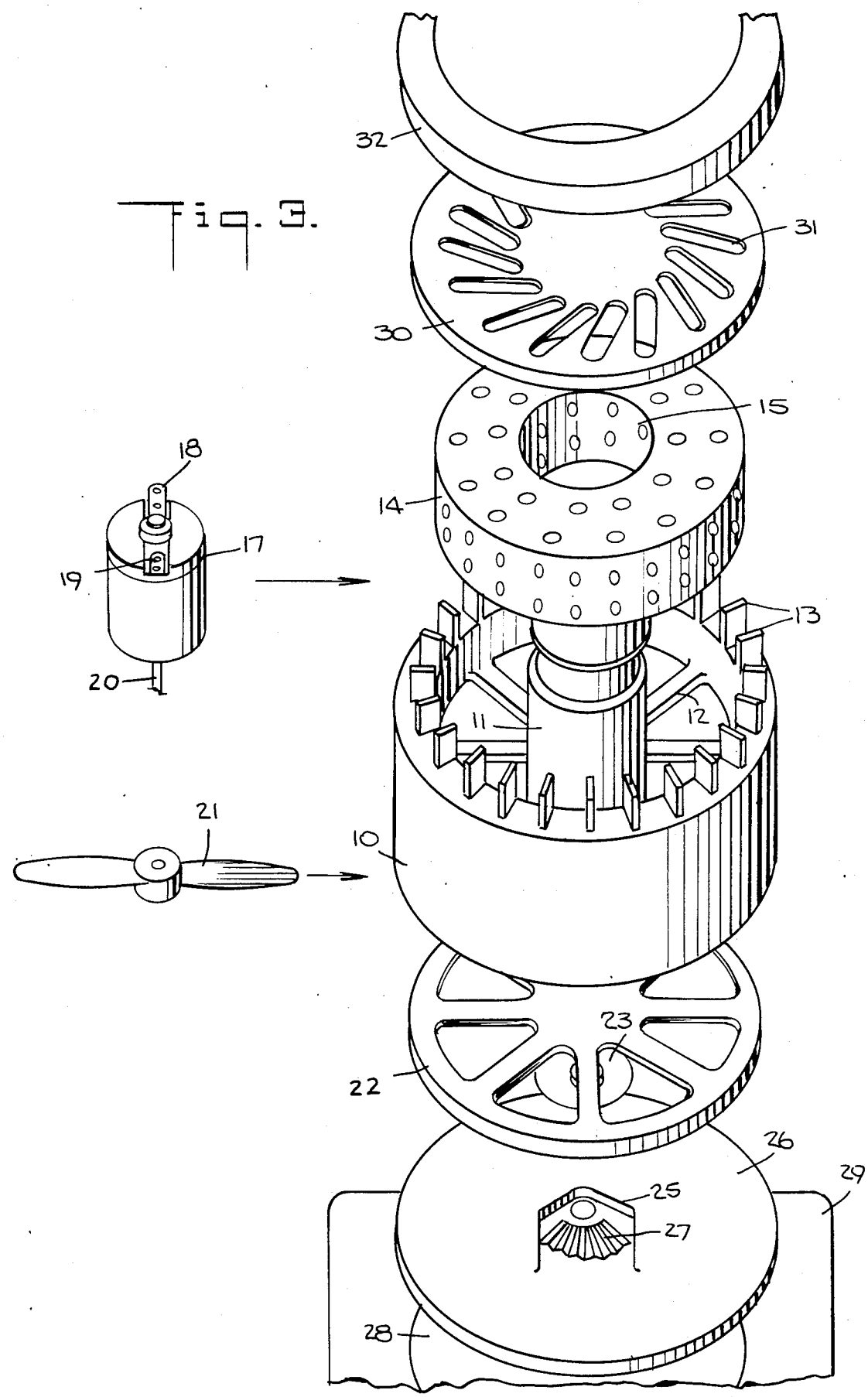

LIGHT-ACTIVATED AROMA GENERATOR

RELATED APPLICATIONS

This application is a continuation-in-part of my co-pending application Ser. No. 592,915 filed March 23, 1984, entitled "Solar Powered Aroma Generator" now U.S. Pat. 4,568,521, issued Feb. 6, 1986.

BACKGROUND OF THE INVENTION

Field of Invention

This invention relates generally to aroma generators, and more particularly to a fan-operated aroma generator that is automatically rendered operative when a light bulb in the room in which the generator is installed is switched on, the generator being otherwise deactivated.

In order to modify the atmosphere of a room, it is knonw to discharge therein air fresheners, deodorizers or aromatic vapors which function to mask or supplant the prevailing odor and render it more agreeable. As used herein, the term "aroma" is generic to all such air modifiers; it is not limited to pleasing fragrances or perfumes, and encompasses various scents or odors that act in some way to modulate the atmosphere of a room.

Certain types of air fresheners are appropriate to heavily-used lavatories and bathrooms, or rooms whose atmosphere is contaminated by tobacco smoke or cooking odors. In other instances, as in bedrooms, a perfumed environment may be more suitable. Hence the effect sought when modifying an atmosphere depends on its initial state and the desired state.

To satisfy the requirements for improving or modifying the atmosphere to create a more agreeable environment, it is known, as in the Koritz U.S. Pat. No. 4,102,656, to blow air through a filter saturated with an aromatic liquid compound, use being made of a motor-driven fan for this purpose. Along similar lines, is the air purifier disclosed in the Madjar U.S. Pat. No. 4,078,891 in which a blower forces air through a filter impregnated with a disinfectant or perfume.

The above-identified patents make use of fan motors energized from a power line, whereas in the Corris U.S. Pat. No. 3,990,848 the fan which forces air through a porous cartridge containing a room deodorizer or germicide is battery-operated.

In order to activate the air purifier at different times and for different intervals, the above-identified Madjar patent provides a timed switch for this purpose. Also of interest is the Boydjieff U.S. Pat. No. 2,614,820, showing a portable vapor-projecting device for perfuming the air and including a timer switch to drive the fan motor for a preset interval. But the timing of this operation is preset and does not depend on unpredictable random actions. Thus in the case of the typical bathroom, there is no way of knowing in advance when the bathroom will be occupied or for how long.

One could, of course, provide an aroma generator of the types disclosed in the above-noted patents with a conventional power switch, so that each time a person enters a room in which the generator is installed, he could turn on the generator, and before leaving the room he could switch it off.

There are, however, several drawbacks incident to the use of such conventional control switches. Thus when a home bathroom is used by a guest, the guest may not know that an aroma generator is installed therein, particularly if the generator is so designed as to assume the appearance of an ornamental object rather than a utilitarian device.

But even if the guest or a resident in the home knows that an aroma generator is installed in the bathroom and turns it on when entering the room, he may thereafter forget to turn it off when leaving. Should the aroma generator then continue to operate, the accumulated amount of aroma then exuded into the atmosphere may be so great as to cause it to spill into adjacent areas or rooms where the bathroom aroma is altogether inappropriate. Moreover, continuous operation of the aroma generator will shorten the effective life of whatever cartridge or pad is used as the aroma supply.

A more serious drawback of aroma generators which derive their power from a high-voltage power line and therefore have to be plugged into the line, is that such devices present a possible electrical hazard in a bathroom where water in some form is inevitably present, and where an individual standing on a wet floor or in a tub, should he then touch the aroma generator, may receive an electrical shock. It is for this reason that battery-operated aroma generators are preferable for bathroom environments.

In my above-identified copending application there is disclosed an aroma generator that is automatically activated when one turns on an electric light bulb in the room in which the generator is installed, the generator then functioning to discharge an air current into the room conveying an aromatic vapor which modifies the prevailing atmosphere.

Included in the generator is a motor-driven fan that forces air through an air permeable cartridge containing an aroma supply, the motor being powered by a solar cell assembly mounted adjacent the bulb. The arrangement is such that when the bulb is switched on, the resultant solar cell output is then sufficient to power the motor and activate the generator. The cell output, in response to ambient light, is insufficient for this purpose; hence the operation of the generator is coordinated with that of the bulb without any wire connection therebetween.

The practical difficulty with the arrangement disclosed in my copending application is that in order to provide sufficient power to operate the motor, the solar cell assembly therefor must have a capacity adequate for this purpose, for the solar cell not only acts effectively as a switch to turn on the motor when the light bulb is switched on, but it also functions as the power source for the motor. A solar cell suitable for this purpose is relatively expensive and adds substantially to the cost of the aroma generator.

SUMMARY OF INVENTION

In view of the foregoing, the main object of this invention is to provide an aroma generator having a battery-powered fan motor that is automatically rendered operative when an electric light source which is disposed at a position adjacent the generator is switched on, the generator otherwise being deactivated.

More particularly, an object of the invention is to provide an aroma generator of the above type which includes a light sensor which controls the operation of the battery-powered motor, the light sensor being adapted to intercept light from the source.

A significant feature of the invention lies in the use of an air-permeable cartridge filled with fragrance beads which exude an aroma at a relatively high rate when an air current is blown therethrough by the fan and which continues to exude an aroma at a much lower rate when the fan is deactivated whereby the aroma generator maintains a low level of fragrance in the room which is stepped up to a high level only when the fan is operated.

Also an object of the invention is to provide a cartridge type aroma generator in which the cartridge, when exhausted, may readily be replaced by a fresh cartridge yielding the same or a different aroma.

Briefly stated, these objects are attained in an aroma generator that is rendered operative only when one turns on an electric light bulb in the room in which the generator is installed, the generator then functioning to discharge an air current into the room conveying an aromatic vapor which modifies the prevailing atmosphere. Included in the generator is a motor-driven fan that forces air through an air-permeable cartridge containing an aroma supply, the motor being connected to a battery through a signal-responsive electronic relay. Applied to the relay is a signal derived from a light sensor which is adjacent the light source to intercept light rays therefrom. The arrangement is such that when the bulb is switched on, the signal from the sensor is then of sufficient magnitude to actuate the relay and thereby render the generator operative, whereby the operation of the aroma generator is coordinated with that of the bulb without any wire connection therebetween.

OUTLINE OF DRAWINGS

For a better understanding of the invention as well as other objects and further features thereof, reference is made to the following detailed description to be read in conjunction with the accompanying drawings, wherein:

FIG. 1 is a sectional view of an aroma generator in accordance with the invention;

FIG. 2 is a side view of the aroma generator when mounted on a wall;

FIG. 3 is an exploded view of the aroma generator; and

FIG. 4 is a schematic diagram of the generator.

DESCRIPTION OF INVENTION

Referring now to FIGS. 1, 2 and 3, an aroma generator in accordance with the invention includes a cylindrical case 10 having a tubular socket 11 supported coaxially therein by a spider 12. Projecting from the front edge of the case is a circular array of fins 13. This structure and all other components are preferably molded from synthetic plastic material having good physical properties, such as polypropylene, polyvinyl chloride or ABS.

Seated on spider 12 within case 10 is a replaceable fragrance cartridge 14 having a circular center hole 15 through which socket 11 extends. The cartridge walls are foraminated so that the cartridge is permeable to air. The cartridge is filled with a charge of fragrance beads 16 of the type commonly used in commercial air fresheners, the fragrance being exuded from the beads at a rate determined by air flow through the air-permeable cartridge. Thus in the absence of forced air flow, the rate of exudation is relatively slow and the cartridge has an extended effective life.

The invention is not limited to fragrance beads, for any aromatic supply may be used in the cartridge, such as a porous pad impregnated with a liquid fragrance. Nor is the invention limited to any particular aroma, and use may be made of deodorizers, air fresheners, perfumes or any other atmosphere-modifying agent.

Received within tubular socket 11 is a miniature low-voltage direct-current motor 17 in cylindrical form having a pair of terminals 18 and 19 at one end and a central shaft 20 projecting from the other end. Supported on this shaft is a propeller fan 21 which rotates within the rear end of body 10 behind spider 12, the back being closed by a closure plaate 22 having a spoked wheel formation.

Closure plate 22 is provided at its rear with a semi-circular tab 23 which projects from the hub of the plate. Tab 23 is attached by a pivot pin 24 to a stud 25 projecting from the front face of a mounting disc 26. One side of stud 25 is provided with a radial array of ridges 27 which frictionally engage the corresponding side of swivel tab 23 to resist displacement of the swivel.

The rear face of mounting disc 26 has attached thereto a layer 28 of pressure-sensitive adhesive material, making it possible to mount the generator at any desired site on a wall 29 adjacent a light bulb B which in practice may be any light bulb in a bathroom or other facility. Because of the swivel, the generator may be oriented relative to the wall to optimize its effectiveness. Thus if the generator is mounted at an elevated position on the wall, it may then be tilted down to direct the aroma toward the occupants of the room.

The front face of cartridge 14 is covered by a disc 30 having an array of vents 31 therein. This disc is held in place by a cover ring 32 which engages the upper portions of fins 13 on the main body 10, the lower portions being exposed to permit aromatic vapors to be discharged omnidirectionally from the circular periphery of the cartridge.

The terminals 18 and 19 of motor 17 are connected to a battery 33 which is housed in a compartment 34 integral with case 10, the connection between the battery and the motor being in series with a signal-responsive solid state electronic relay 35 disposed within the case, so that the motor is powered only when the relay is actuated.

Applied to the relay 35 is a signal derived from a light sensor 36 which is disposed within an orientable ball joint 37 on the side of the casing, so that the sensor may be oriented to pick up light rays from bulb B regardless of where it is mounted on the wall relative to the bulb.

The electronic relay 35 may be any solid state switching device such as a transistor circuit which is rendered conductive when a signal is applied to its control or gate element exceeding a threshold level. Various types of such electronic relays are disclosed in Section 15 of the *Electronics Engineers' Handbook,* D. G. Fink, McGraw-Hill Book Co., first edition.

The light sensor 36 may be a photovoltaic sensor such as a selenium or silicon cell which generates an output signal as a function of the illumination incident thereto, or it may be in the form of a photoconductive function semi-conductor or phototransistor. Regardless of the type of light sensor used, its relationship to the electronic relay is such that the relay is actuated only when the light incident to the sensor is at an intensity well above that of ambient natural light in the room.

Thus while there may be ambient natural light in the room which will result in some signal output from the light sensor, the relationship is such that this output is insufficient to actuate the electronic relay and power the motor. As a consequence, when the light bulb or other light source such as a fluorescent lamp is turned off, the generator exudes only a low level of aroma, for the fan is not then operative and no air is then forced through the cartridge. This low level in the static condition of the generator acts to prime the atmosphere of the room, but little aroma seepage from the room takes place even if the door is open; for the fragrance in the atmosphere is diluted. But when one enters the room and turns on the light, then the motor is automatically energized and the fan drives a current of air through the cartridge, which current is discharged into the atmosphere and carries with it an aromatic vapor to step up the fragrance in the room to a high level. The moment, however, the light is turned off, this discharge is discontinued.

While there has been shown and described a preferred embodiment of a LIGHT-ACTIVATED AROMA GENERATOR in accordance with the invention, it will be appreciated that many changes and modifications may be made therein without, however, departing from the essential spirit thereof.

I claim:

1. In combination with a switch-controlled light bulb disposed at a fixed position in a room having ambient light therein, an aroma generator which is rendered operative to modify the atmosphere of the room only when the switch connected to said light bulb is turned on; said generator comprising:
   A. a case having pressure-sensitive adhesive mounting means for mounting the case on a wall in the room at a position adjacent the light bulb and including a compartment for housing of a battery;
   B. a low-voltage direct current motor coupled to a propeller fan and which is housed in said case;
   C. an orientable light sensor mounted on said case, said sensor being orientable relative to said light bulb to intercept light rays from said light bulb to produce a signal whose magnitude depends on the intensity of the rays impinging thereon;
   D. an air permeable cartridge containing an aroma supply and disposed in said case in operative relation to said fan to exude an aroma into the atmosphere at a relatively rapid rate only when an air current is forced through said cartridge by said fan; and
   E. a signal-responsive electronic relay disposed in said case, said relay being coupled to said sensor and connecting said battery to said motor, said relay being actuated only when the signal applied thereto by said sensor has a magnitude which is a function of the light rays from the bulb when it is switched on and substantially exceeds the magnitude of the signal resulting from said ambient light, whereby the operation of the generator is coordinated with that of the light bulb, despite the absence of a wired connection therebetween and the generator is rendered operative only when the switch is turned on.

2. The combination as set forth in claim 1, wherein said case is cylindrical and said cartridge is received in a front end of the case.

3. The combination as set forth in claim 2, wherein the aroma supply is constituted by a charge of fragrance beads.

4. The combination as set forth in claim 3, wherein said motor is cylindrical and is coaxially disposed within said case, the base being behind the cartridge.

5. The combination as set forth in claim 3, further including a vented closure at the rear end of the case.

6. The combination as set forth in claim 1, wherein said electronic relay is a transistor.

7. The combination as set forth in claim 6, wherein said light sensor is a photodiode.

* * * * *